(12) United States Patent
Hagihara et al.

(10) Patent No.: US 11,955,498 B2
(45) Date of Patent: Apr. 9, 2024

(54) IMAGE PICKUP APPARATUS, ENDOSCOPE, AND METHOD OF MANUFACTURING IMAGE PICKUP APPARATUS

(71) Applicant: OLYMPUS CORPORATION, Tokyo (JP)

(72) Inventors: Mitsuru Hagihara, Nagano (JP); Takuro Suyama, Ina (JP)

(73) Assignee: OLYMPUS CORPORATION, Tokyo (JP)

(*) Notice: Subject to any disclaimer, the term of this patent is extended or adjusted under 35 U.S.C. 154(b) by 154 days.

(21) Appl. No.: 17/864,678

(22) Filed: Jul. 14, 2022

(65) Prior Publication Data
US 2022/0352233 A1 Nov. 3, 2022

Related U.S. Application Data

(63) Continuation of application No. PCT/JP2020/002065, filed on Jan. 22, 2020.

(51) Int. Cl.
| | | |
|---|---|---|
| H01L 27/146 | (2006.01) |
| A61B 1/04 | (2006.01) |
| G02B 23/24 | (2006.01) |
| H04N 23/50 | (2023.01) |
| H04N 23/51 | (2023.01) |

(Continued)

(52) U.S. Cl.
CPC .......... *H01L 27/14632* (2013.01); *A61B 1/04* (2013.01); *G02B 23/2484* (2013.01);

(Continued)

(58) Field of Classification Search
CPC . H01L 27/14632; H01L 27/1469; A61B 1/04; A61B 1/051; A61B 1/0011;

(Continued)

(56) References Cited

U.S. PATENT DOCUMENTS

| | | | | |
|---|---|---|---|---|
| 4,918,521 A | * | 4/1990 | Yabe | H04N 23/54 |
| | | | | 600/109 |
| 7,679,669 B2 | * | 3/2010 | Kwak | H04N 23/57 |
| | | | | 348/340 |

(Continued)

FOREIGN PATENT DOCUMENTS

| | | |
|---|---|---|
| EP | 3 313 063 A1 | 4/2018 |
| JP | H05-261065 A | 10/1993 |

(Continued)

OTHER PUBLICATIONS

International Search Report dated Mar. 10, 2020 received in PCT/JP2020/002065.

*Primary Examiner* — Shahbaz Nazrul
(74) *Attorney, Agent, or Firm* — Scully, Scott, Murphy & Presser, P.C.

(57) ABSTRACT

An image pickup apparatus includes an image pickup member including an image pickup device, a stacked device in which a plurality of semiconductor devices are stacked, a wiring board having a first principal surface and a second principal surface, the wiring board including a central section having a substrate thicker than the image pickup device, an intermediate section that is extended from the central section and is bent, and a terminal section that is extended from the intermediate section, the image pickup member being bonded to the first principal surface of the central section, the stacked device being bonded to the second principal surface of the central section, and a plurality of signal cables bonded to the terminal section.

15 Claims, 8 Drawing Sheets

(51) Int. Cl.
*H04N 23/54* (2023.01)
*A61B 1/05* (2006.01)

(52) U.S. Cl.
CPC ......... *H01L 27/1469* (2013.01); *H04N 23/51* (2023.01); *H04N 23/54* (2023.01); *A61B 1/051* (2013.01); *H04N 23/555* (2023.01)

(58) Field of Classification Search
CPC .... G02B 23/2484; H04N 23/51; H04N 23/54; H04N 23/555; H04N 23/57
See application file for complete search history.

(56) References Cited

U.S. PATENT DOCUMENTS

| | | | |
|---|---|---|---|
| 10,510,918 B2* | 12/2019 | Hu | H01L 31/0203 |
| 10,750,940 B2* | 8/2020 | Kawayoke | H04N 23/00 |
| 10,925,464 B2* | 2/2021 | Sekido | H04N 23/50 |
| 2018/0049627 A1* | 2/2018 | Adachi | G02B 23/26 |
| 2019/0175003 A1* | 6/2019 | Yoshida | H04N 23/57 |
| 2020/0344386 A1* | 10/2020 | Yamamoto | H01L 27/14618 |

FOREIGN PATENT DOCUMENTS

| | | |
|---|---|---|
| JP | 4441305 B2 | 3/2010 |
| JP | 4575698 B2 | 11/2010 |
| JP | 2011-217887 A | 11/2011 |
| JP | 2013-219511 A | 10/2013 |
| JP | 2015-231558 A | 12/2015 |
| WO | 2015/019671 A1 | 2/2015 |
| WO | 2016/203828 A1 | 12/2016 |
| WO | 2017/073440 A1 | 5/2017 |

* cited by examiner

IMAGE PICKUP APPARATUS, ENDOSCOPE, AND METHOD OF MANUFACTURING IMAGE PICKUP APPARATUS

CROSS REFERENCE TO RELATED APPLICATION

This application is a continuation application of PCT/JP2020/002065 filed on Jan. 22, 2020, the entire contents of which are incorporated herein by this reference.

BACKGROUND OF THE INVENTION

1. Field of the Invention

The invention relates to an image pickup apparatus including a stacked device, an endoscope including an image pickup apparatus including a stacked device, and a method of manufacturing an image pickup apparatus including a stacked device.

2. Description of the Related Art

An image pickup signal outputted from an image pickup device is processed by a plurality of electronic components, and is transmitted. International Publication No. WO 2016/203828 discloses an endoscope that achieves size reduction and increased functionality of an image pickup apparatus by using a stacked device in which a plurality of semiconductor devices are stacked.

In an image pickup unit of FIG. 3 of the above publication, the stacked device is arranged at a back portion of a wiring board that is bonded to a rear surface of the image pickup device and is extended backward. Thus, the above-described image pickup unit has a long dimension in an optical axis direction. On the other hand, an image pickup unit of FIG. 4 of the above publication has a short dimension in the optical axis direction because the stacked device is bonded to the rear surface of the image pickup device.

SUMMARY OF THE INVENTION

An image pickup apparatus of an embodiment includes: an image pickup member including an image pickup device; a stacked device in which a plurality of semiconductor devices are stacked; a wiring board including a first principal surface and a second principal surface opposite to the first principal surface, the wiring board including a central section including a substrate thicker than the image pickup device, at least one intermediate section that is extended from the central section and is bent, and at least one terminal section that is extended from the intermediate section, the image pickup member being bonded to the first principal surface of the central section, the stacked device being bonded to the second principal surface of the central section; and a plurality of signal cables bonded to the terminal section.

An endoscope of an embodiment includes an image pickup apparatus, in which the image pickup apparatus includes: an image pickup member including an image pickup device; a stacked device in which a plurality of semiconductor devices are stacked; a wiring board including a first principal surface and a second principal surface opposite to the first principal surface, the wiring board including a central section including a substrate thicker than the image pickup device, at least one intermediate section that is extended from the central section and is bent, and at least one terminal section that is extended from the intermediate section, the image pickup member being bonded to the first principal surface of the central section, the stacked device being bonded to the second principal surface of the central section; and a plurality of signal cables bonded to the terminal section.

A method of manufacturing an image pickup apparatus of an embodiment includes: fabricating an image pickup member including an image pickup device, a stacked device in which a plurality of semiconductor devices are stacked, and a wiring board including a first principal surface and a second principal surface opposite to the first principal surface, the wiring board including a central section including a substrate thicker than the image pickup device, an intermediate section that is extended from the central section, and a terminal section that is extended from the intermediate section; bonding the stacked device to the second principal surface of the central section of the wiring board; bending the intermediate section into a state that covers a side surface of the stacked device, and securing the intermediate section; bonding the image pickup member to the central section of the wiring board; and bonding a plurality of signal cables to the terminal section.

DETAILED DESCRIPTION OF THE PREFERRED EMBODIMENTS

Configuration of Endoscope

Figure 1:
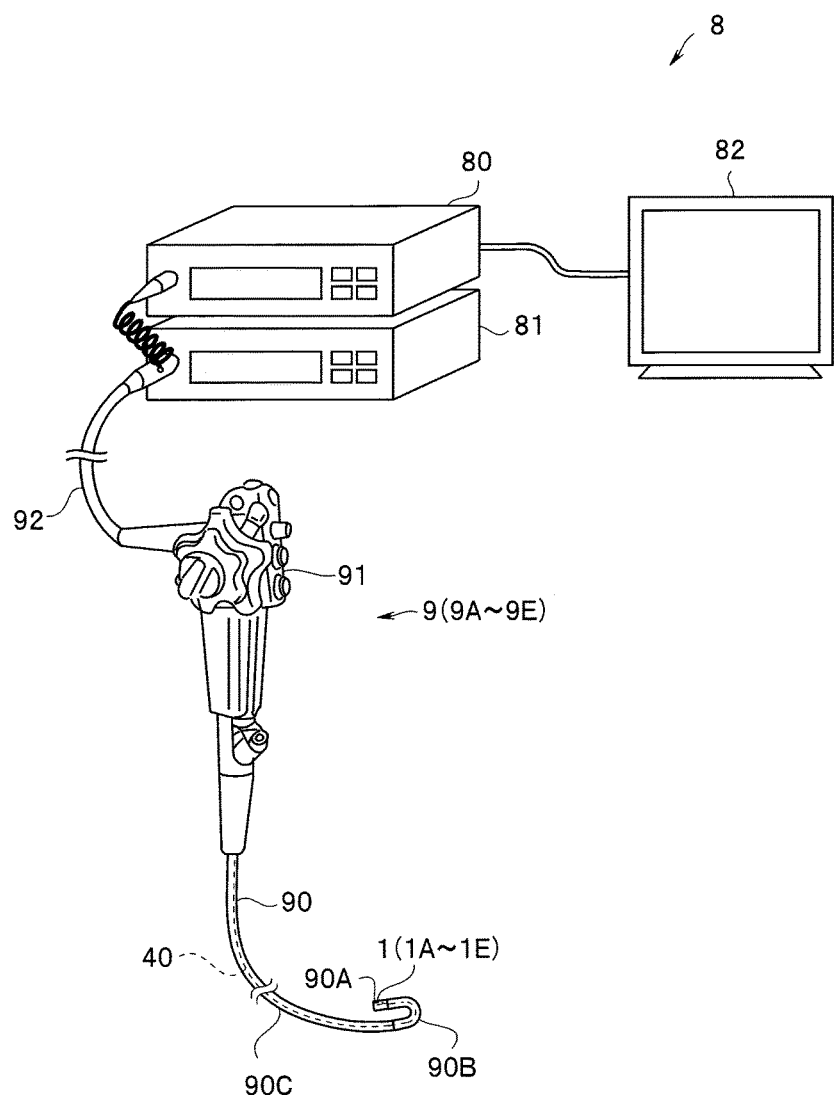
FIG. 1 is an external view of an endoscope of an embodiment.

An endoscope system 8 shown in FIG. 1 includes an endoscope 9 of an embodiment, a processor 80, a light source device 81, and a monitor 82. The endoscope 9 has an insertion section 90, an operation section 91, and a universal cord 92. The endoscope 9 picks up an image in the body of a subject with the insertion section 90 inserted into the body, and outputs an image pickup signal.

The insertion section 90 is composed of a distal end portion 90A on which an image pickup apparatus 1 is disposed, a bending portion 90B that is continuously connected with the distal end portion 90A and can be bent, and a flexible portion 90C that is continuously connected with the bending portion 90B.

The operation section 91 provided with various buttons for operating the endoscope 9 is disposed at a proximal end portion of the insertion section 90 of the endoscope 9. The bending portion 90B is bent in response to an operation of the operation section 91.

The light source device 81 has a white LED, for example. Illumination light emitted from the light source device 81 is guided to the distal end portion 90A by way of a light guide (not shown) inserted through the universal cord 92 and the insertion section 90, and illuminates the subject.

The processor 80 controls the endoscope system 8 as a whole, and subjects the image pickup signal outputted from the image pickup apparatus 1 to signal processing to output an image signal. The monitor 82 displays the image signal outputted from the processor 80 as an endoscope image.

As will be described later, the image pickup apparatus 1 is compact, and enables a high-quality image to be obtained. The endoscope 9 is less invasive because of a small diameter, and enables a high-quality image to be obtained.

Note that although the endoscope 9 is a flexible endoscope for medical use, the endoscope of the invention may be a rigid endoscope, and may be applied to industrial use.

First Embodiment

Figure 2:
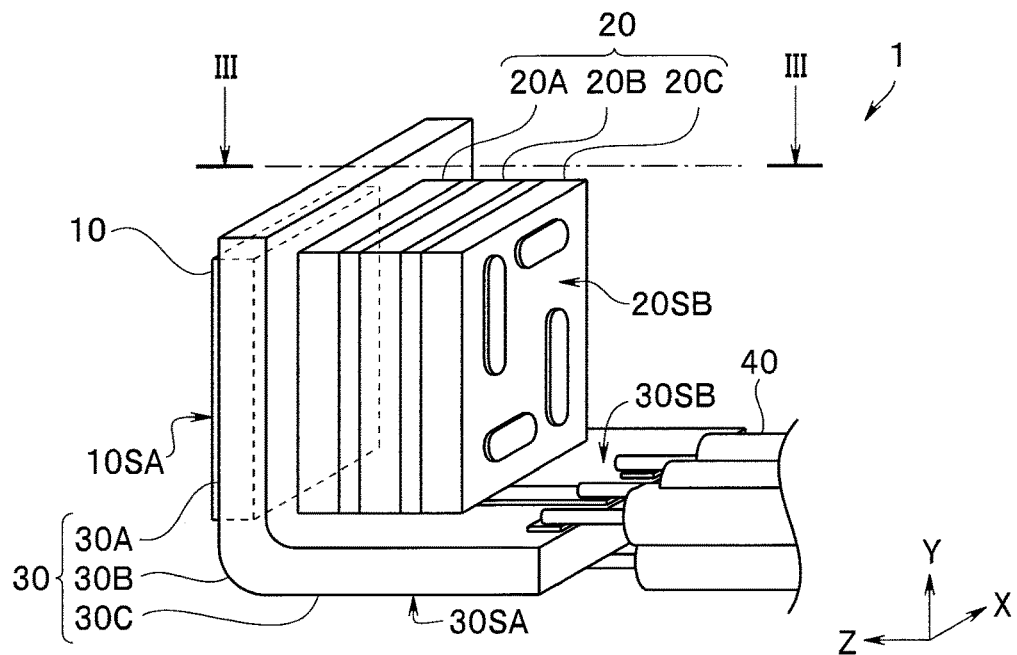
FIG. 2 is a perspective view of an image pickup apparatus of a first embodiment.
Figure 3:
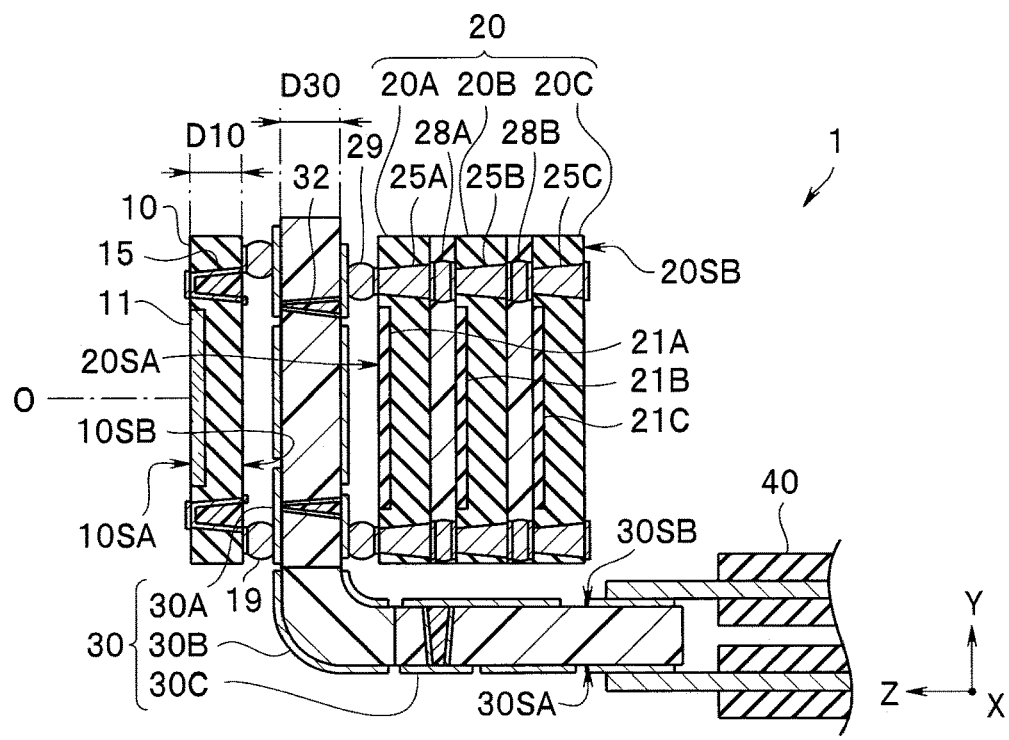
FIG. 3 is a cross-sectional view of the image pickup apparatus of the first embodiment taken along the line III-III of FIG. 2.
Figure 4:
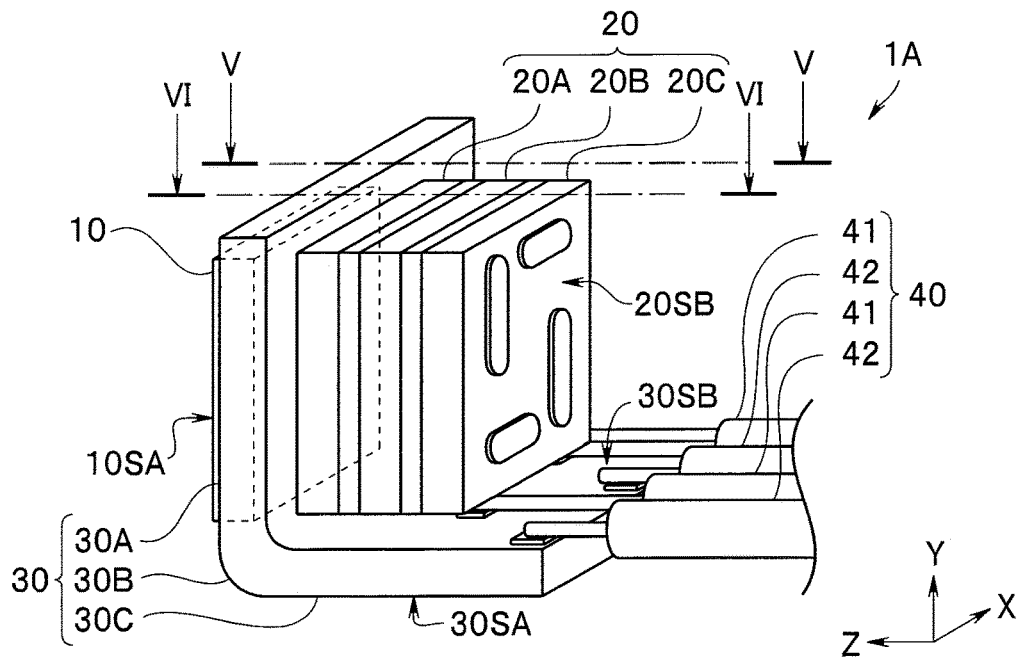
FIG. 4 is a perspective view of an image pickup apparatus of a second embodiment.

The image pickup apparatus 1 of the present embodiment shown in FIG. 2 and FIG. 3 includes an image pickup device 10, a stacked device 20, a wiring board 30, and signal cables 40.

Note that the drawings based on the respective embodiments are schematic views. A relationship between a thickness and a width of each portion, a ratio between thicknesses, relative angles and the like of respective portions are different from the actual ones. Some portions are described in different size relationships or at different ratios among the drawings. Illustration of some components and the indication of components by reference characters are omitted. A direction in which a subject is located along an optical axis O is referred to as "front".

The image pickup device (imager) 10 has a light receiving circuit 11 implemented by a CCD or a CMOS on a light receiving surface 10SA. Although not shown in FIG. 2 and the like, a cover glass 52 and an image pickup optical system 53 are disposed on the light receiving surface 10SA (see FIG. 10). On a rear surface 10SB opposite to the light receiving surface 10SA of the image pickup device 10, a bonding conductor 19 connected to the light receiving circuit 11 with the interposition of a through wiring 15 extending through in a thickness direction is disposed.

The stacked device 20 has a bonding surface 20SA and a back surface 20SB opposite to the bonding surface 20SA. The stacked device 20 is a substantially rectangular parallelepiped shape member in which a plurality of semiconductor devices 20A, 20B, and 20C are stacked. Through wirings 25A to 25C that extend through in the thickness direction of the semiconductor devices 20A to 20C opposite to one another are bonded by bonding conductors 28A and 28B, respectively. A plurality of bonding conductors 29 are disposed on the bonding surface 20SA which is a surface of the stacked device 20 that is proximate to the image pickup device 10.

For example, the bonding conductors 19, 28A, 28B, and 29 are stud bumps, plated bumps, or ball bumps having a height of 10 µm to 100 µm and made of gold or solder.

The image pickup device 10 and the semiconductor devices 20A to 20C are flat semiconductor chips each having a silicon substrate. Semiconductor circuits 21A to 21C are formed in the semiconductor devices 20A to 20C, respectively.

The wiring board 30 has a first principal surface 30SA and a second principal surface 30SB opposite to the first principal surface 30SA. The wiring board 30 has a substrate and a wiring formed of conductor layers disposed on both the first principal surface 30SA and the second principal surface 30SB. The substrate contains resin, for example, and may also contain air as will be described later. The wiring board 30 may have insulating resin layers that cover the conductor layers, or may be a multi-layer wiring board.

The wiring board 30 includes a central section 30A, a bent intermediate section 30B, and a terminal section 30C to which the signal cables 40 are bonded. The intermediate section 30B is extended from one of the four sides of the central section 30A which is a flat, substantially rectangular region. The terminal section 30C is further extended from the intermediate section 30B. Since the central section 30A, the intermediate section 30B, and the terminal section 30C have the same width, the wiring board 30 in a state in which the intermediate section 30B is not bent is rectangular flat plate.

The wiring board 30 is a rigid-flexible wiring board in which the central section 30A and the terminal section 30C have rigid substrates, and the intermediate section 30B has a flexible substrate.

The rear surface 10SB of the image pickup device 10 is bonded to the first principal surface 30SA of the central section 30A. The bonding surface 20SA of the stacked device 20 is bonded to the second principal surface 30SB of the central section 30A. In other words, the plurality of semiconductor devices 20A to 20C of the stacked device 20 are stacked in the optical axis direction. Note that the stacked device 20 is preferably provided at a position corresponding to the image pickup device 10 on the second principal surface 30SB of the central section 30A.

Note that, for example, an image pickup member having one or more semiconductor devices bonded to the rear surface 10SB of the image pickup device 10 may be bonded to the wiring board 30. In other words, the image pickup apparatus 1 may have an image pickup member including at least the image pickup device 10.

In the wiring board 30, the intermediate section 30B is bent at an angle of substantially 90 degrees, for example, 70 degrees or more and 110 degrees or less. Thus, the terminal section 30C arranged substantially parallel to a side surface of the stacked device 20 and the central section 30A form an angle of substantially 90 degrees. Note that part of the terminal section 30C may be in contact with the side surface of the stacked device 20.

The plurality of signal cables 40 are bonded to wirings of the first principal surface 30SA and the second principal surface 30SB at a back end portion of the terminal section 30C. In other words, a region to which the signal cables 40 are bonded is the terminal section 30C of the wiring board 30.

Note that the plurality of signal cables 40 should only be bonded to at least either the first principal surface 30SA or the second principal surface 30SB. The signal cables 40 may be shielded cables. In addition, resin (not shown) that secures a bent state of the intermediate section 30B may be disposed between the stacked device 20 and the wiring board 30.

The image pickup apparatus 1 has a short length in the optical axis direction and is compact because of the structure in which the image pickup device 10 and the stacked device 20 are stacked with the interposition of the wiring board 30 (the central section 30A).

As already described, the stacked device 20 generates heat. For example, when heat generated by a drive signal generating circuit of the semiconductor device is transferred to the image pickup device 10, a high-quality image may not be obtained.

However, in the image pickup apparatus 1, the central section 30A which is a heat insulation member is arranged between the image pickup device 10 and the stacked device 20. Thus, heat of the stacked device 20 is unlikely to be transferred to the image pickup device 10.

Epoxy resin, for example, is used as the material of the substrate of the central section 30A. The heat conductivity of epoxy resin is 0.35 W/m·K, which is much smaller than 400 W/m·K which is the heat conductivity of copper as a conductor, Thus, a large part of heat of the stacked device 20 is transferred to the signal cables 40 by way of the conductor layer provided on the second principal surface 30SB of the wiring board 30. A large part of heat of the image pickup device 10 is transferred to the signal cables 40 by way of the conductor layer provided on the first principal surface 30SA of the wiring board 30.

Resin having a heat conductivity of 1 W/m·K or less is preferable as the material of the substrate of the wiring board 30. Preferable examples of the material of the substrate of the wiring board 30 include epoxy resin, polyimide resin, fluorine resin, polyamide-imide, polyphenyleneether, polypropylene, polysulfone, polyethersulfone, polyetheretherketone, polyetherketone, polyetherimide, fluorine-based thermoplastic elastomer, and butadiene-based rubber.

Note that since the central section 30A has the through wiring 32 that extends through in the thickness direction, part of heat generated by the stacked device 20 is transferred to the image pickup device 10 by way of the through wiring 32 and the through wiring 15 of the image pickup device 10. However, the through wiring 32 and the through wiring 15 are what is called conformal vias in each of which a conductor layer is disposed on a wall surface of a through hole and the inside is filled with resin. The conformal via has a thermal resistance higher than the thermal resistance of what is called a filled via having a through hole filled with a conductor. The thermal resistance is a parameter indicating unlikelihood of heat transfer from one principal surface to the other principal surface of a flat plate. Thus, heat is hardly transferred from the stacked device 20 to the image pickup device 10 by way of the through wiring 32 and the through wiring 15 of the image pickup device 10.

Resin of the substrate of the central section 30A preferably contains 10% by volume of air or more. Since the heat conductivity of air is as extremely small as 0.0241 W/m·K, the resin substrate containing air has a large thermal resistance. Note that in order to ensure a mechanical strength, air contained in resin is preferably 70% by volume or less, for example.

The image pickup apparatus 1 has a short length in the optical axis direction, and is compact. The image pickup apparatus 1 enables a high-quality image to be obtained since heat of the stacked device 20 is unlikely to be transferred to the image pickup device 10.

Note that the thickness of the substrate of at least either the intermediate section 30B or the terminal section 30C is more preferably larger than a thickness D10 of the image pickup device 10. Resin of the substrate of at least either the intermediate section 30B or the terminal section 30C more preferably contains 10% by volume of air or more.

Method of Manufacturing Image Pickup Apparatus

A method of manufacturing the image pickup apparatus 1 will now be described briefly.

<Step S10> Step of Fabricating Components

The image pickup device 10, the stacked device 20, and the wiring board 30 are fabricated.

The image pickup device 10 is fabricated by cutting an image pickup wafer having a plurality of light receiving circuits 11 and the like. The image pickup device 10 may be either a front-illuminated imager or a back-illuminated imager.

The stacked device 20 is fabricated by cutting a stacked wafer in which, for example, semiconductor device wafers respectively having the plurality of semiconductor circuits 21A, 21B, 21C, and the like are stacked, and are bonded to one another with the plurality of bonding conductors 28A and 28B. The semiconductor circuits 21A to 21C process an image pickup signal outputted from the image pickup device 10, and process a control signal that controls the image pickup device 10. The semiconductor devices 20A to 20C each include, for example, an AD conversion circuit, a memory, a transmission and output circuit, a drive signal generating circuit, a filter circuit, a thin-film capacitor, a thin-film inductor, and the like. A plurality of semiconductor circuits may be formed in a single semiconductor device, or semiconductor circuits may be formed respectively on both the principal surfaces of a single semiconductor device. The number of semiconductor devices included in the stacked device 20 is 1 or more and 10 or fewer, for example.

As already described, the wiring board 30 is a rigid-flexible wiring board including the central section 30A which is non-flexible, the intermediate section 30B which is flexible, and the terminal section 30C which is non-flexible. The substrates of the central section 30A and the terminal section 30C are made of a non-flexible resin such as epoxy resin. The substrate of the intermediate section 30B is made of a flexible resin such as polyimide.

The central section 30A, the intermediate section 30B, and the terminal section 30C may be different in thickness or the like. The wiring board 30 is a double sided wiring board having a conductor layer made of copper having a thickness of 1 μm to 10 μm, but may be a multi-layer wiring board also having a wiring in the inside. An electronic component such as a chip capacitor may be mounted on at least either the first principal surface 30SA or the second principal surface 30SB.

<Step S20> Step of Bonding Stacked Device

The stacked device 20 is bonded to the wiring board 30 in a state in which the intermediate section 30B is not bent. More specifically, the stacked device 20 is bonded to the second principal surface 30SB of the central section 30A of the wiring board 30. For example, a solder bump which is the bonding conductor 29 that electrically connects the wiring board 30 and the stacked device 20 is bonded to an electrode of the conductor layer of the second principal surface 30SB.

A gap between the stacked device 20 and the wiring board 30 may be filled with a high thermal conductive resin containing an insulating filler such as silicon particles. For example, silicon has a heat conductivity of 160 W/m·K.

<Step S30> Step of Bending Wiring Board

Bending of the intermediate section 30B at substantially 90 degrees brings about a state in which the terminal section 30C covers the side surface of the stacked device 20. In other words, the terminal section 30C becomes substantially parallel to the side surface of the stacked device 20. Then, resin not shown secures the intermediate section 30B in a bent state.

<Step S40> Step of Bonding Image Pickup Device

The image pickup device 10 is bonded to the first principal surface 30SA of the central section 30A.

For example, a gold bump which is the bonding conductor 19 that electrically connects the image pickup device 10 and the wiring board 30 is bonded by ultrasound to a gold electrode disposed on the conductor layer of the first principal surface 30SA.

Note that although the substrates of all the sections of the wiring board 30 may be flexible, the central section 30A is preferably non-flexible so as to facilitate bonding of the stacked device 20 and the image pickup device 10. On the other hand, the terminal section 30C may be either flexible or non-flexible.

<Step S50> Step of Bonding Cables

The plurality of signal cables 40 are bonded to the back end portion of the terminal section 30C using solder, for example. Note that the cable bonding step may be performed prior to the wiring board bending step or the image pickup device bonding step. Alternatively, bonding of part of the plurality of signal cables 40 may be performed prior to the wiring board bending step or the image pickup device bonding step. In other words, bonding of the signal cables 40 may be performed in any stage of the manufacturing process, or may be performed in a plurality of steps, as long as the wiring board 30 has been manufactured.

However, it is preferable to initially bond a cable or a shielded wire of a shielded cable, which is at a ground potential, among the plurality of signal cables 40 to the wiring board 30 in order to prevent a trouble caused by static electricity from occurring.

Second Embodiment

Since an image pickup apparatus 1A of a second embodiment is similar to the image pickup apparatus 1, components having the same functions are denoted by the same reference characters, and description will be omitted.

In the image pickup apparatus 1A of the present embodiment shown in FIG. 4 to FIG. 8, the wiring board 30 does not have any through wiring in the central section 30A. The image pickup device 10 and the stacked device 20 are connected by way of a through wiring 35 that extends through the terminal section 30C in the thickness direction. The wiring board 30 may have a through wiring in the intermediate section 30B. In other words, the wiring board 30 of the present embodiment has a through wiring only at a place other than the central section 30A.

The plurality of signal cables 40 bonded to the second principal surface 30SB include first cables 41 not bonded to the through wiring 35 and second cables 42 bonded to the through wiring 35.

The plurality of signal cables 40 (41, 42) are bonded only to the second principal surface 30SB. Note that the plurality of signal cables 40 (41, 42) may be bonded only to the first principal surface 30SA. In other words, the plurality of signal cables 40 (41, 42) are bonded only to either the first principal surface 30SA or the second principal surface 30SB. Thus, the image pickup apparatus 1A is easy to manufacture.

Figure 7A:
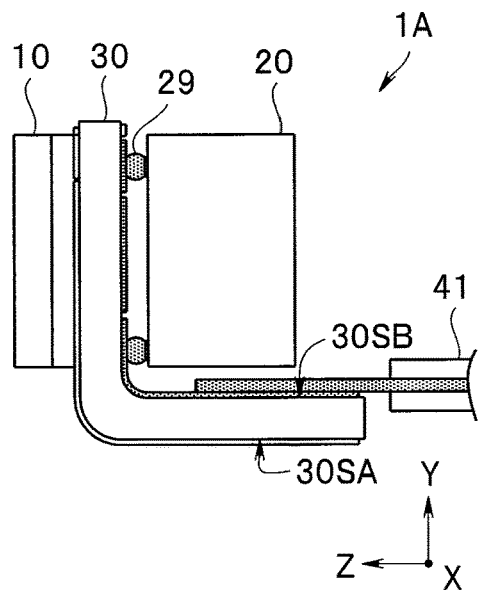
FIG. 7A is a schematic cross-sectional view showing a heat transfer path from a stacked device of the image pickup apparatus of the second embodiment to a signal cable.
Figure 7B:
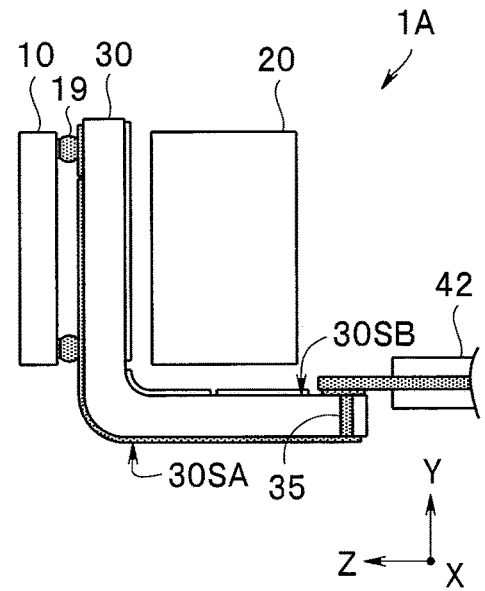
FIG. 7B is a schematic cross-sectional view showing a heat transfer path from the image pickup device of the image pickup apparatus of the second embodiment to a cable.

As shown in FIG. 7A, a large part of heat generated by the stacked device 20 is transferred to the first cables 41 by way of the conductor layer of the second principal surface 30SB. On the other hand, as shown in FIG. 7B, a large part of heat generated by the image pickup device 10 is transferred to the second cables 42 by way of the conductor layer of the first principal surface 30SA and the through wiring 35.

In the image pickup apparatus 1A, a transfer path from the stacked device 20 to the first cables 41 and a transfer path from the image pickup device 10 to the second cables 42 are separated into the two principal surfaces of the wiring board 30. Thus, in the image pickup apparatus 1A, heat of the stacked device 20 is unlikely to be transferred to the image pickup device 10.

Note that distal end portions of the second cables 42 not bonded to the through wiring 35 are preferably bonded to the conductor layer at a position closer to the central section 30A than to the through wiring 35. This is because, with the configuration, heat from the stacked device 20 is transferred to the second cables 42 earlier than to the through wiring 35, and is therefore unlikely to be transferred to the through wiring 35.

Moreover, since the image pickup apparatus 1A does not have a through wiring having a small thermal resistance in the central section 30A, heat of the stacked device 20 is less likely to be transferred to the image pickup device 10 by way of the central section 30A than in the image pickup apparatus 1. Thus, the image pickup apparatus 1A enables a higher quality image to be obtained than the image pickup apparatus 1.

Figure 5:
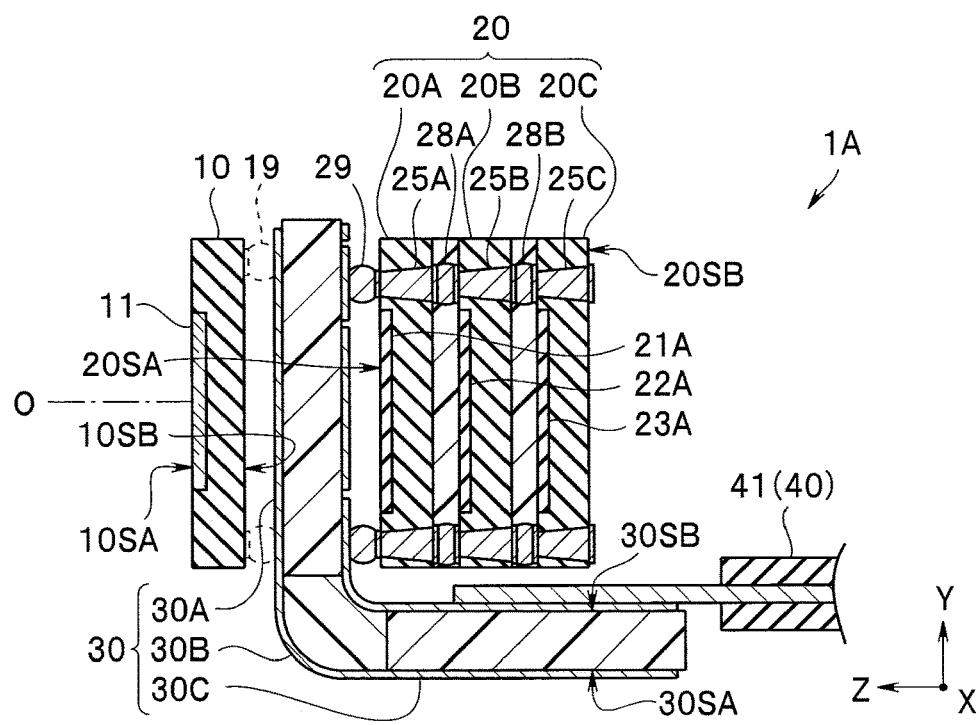
FIG. 5 is a cross-sectional view of the image pickup apparatus of the second embodiment taken along the line V-V of FIG. 4.
Figure 6:
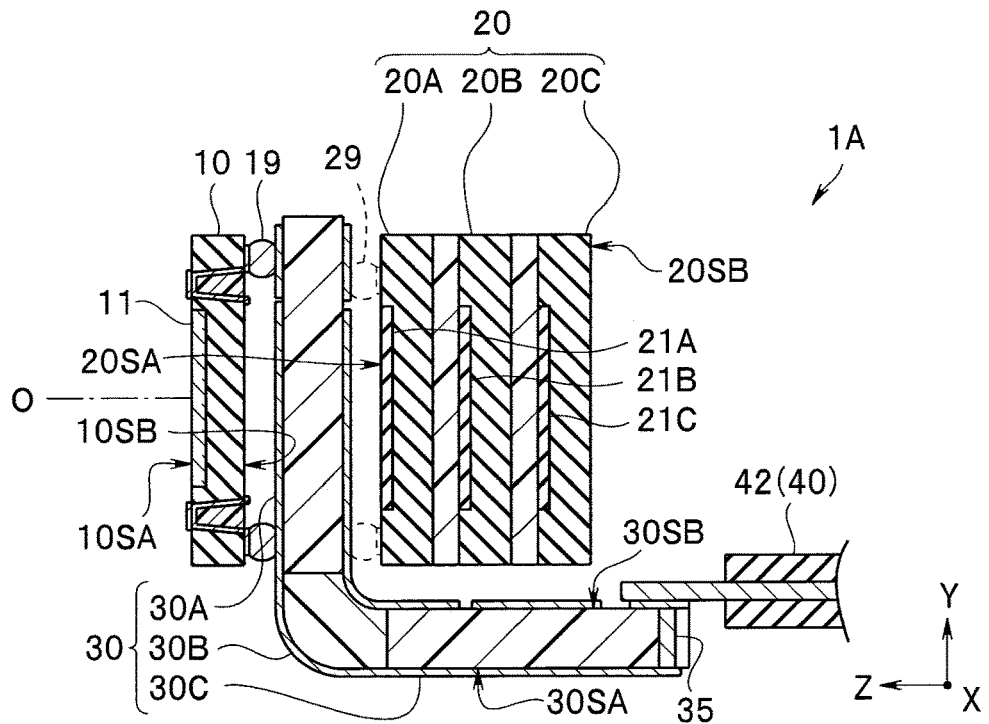
FIG. 6 is a cross-sectional view of the image pickup apparatus of the second embodiment taken along the line VI-VI of FIG. 4.

Furthermore, as shown in FIG. 5 and FIG. 6, the bonding conductor 29 and the bonding conductor 19 do not overlap each other as seen in the thickness direction of the central section 30A. Thus, in the image pickup apparatus 1A, heat of the stacked device 20 is less likely to be transferred to the image pickup device 10 by way of the central section 30A than in the image pickup apparatus 1.

Figure 8:
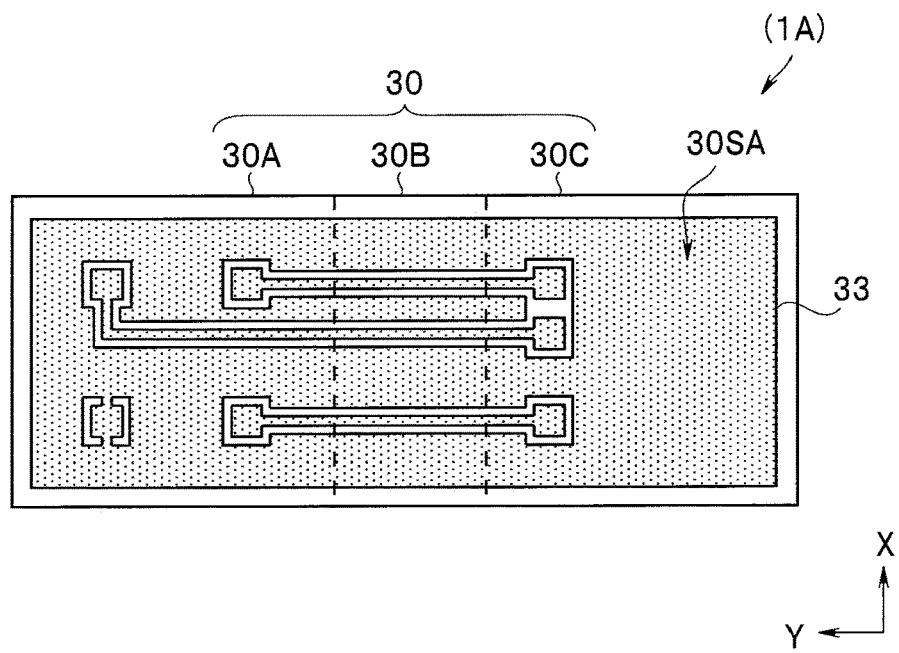
FIG. 8 is a plan view of a wiring board of the image pickup apparatus of the second embodiment.

As already described, main paths along which heat is transferred in the first principal surface 30SA and the second principal surface 30SB of the wiring board 30 are conductor layers having a high heat conductivity and made of copper or the like. In order to make a thermal resistance in a planar direction smaller than a thermal resistance in the thickness direction (the optical axis direction) in the wiring board 30, 70% or more of the first principal surface 30SA and the second principal surface 30SB is preferably covered by a conductor layer 33, as shown in FIG. 8, for example. In other words, the conductor layer 33 may include a dummy pattern having a large area, for example, in addition to a wiring pattern. The dummy pattern is preferably connected to a signal cable or a shielded wire of a shielded cable which is at the ground potential.

Note that it is important to make the thermal resistance in the planar direction small particularly in the central section 30A. Thus, in the wiring hoard 30, 70% or more of at least the first principal surface 30SA and the second principal surface 30SB of the central section 30A is preferably covered by the conductor layer 33.

Third Embodiment

Since an image pickup apparatus 1B of a third embodiment is similar to the image pickup apparatuses 1 and 1A, components having the same functions are denoted by the same reference characters, and description will be omitted.

Figure 9:
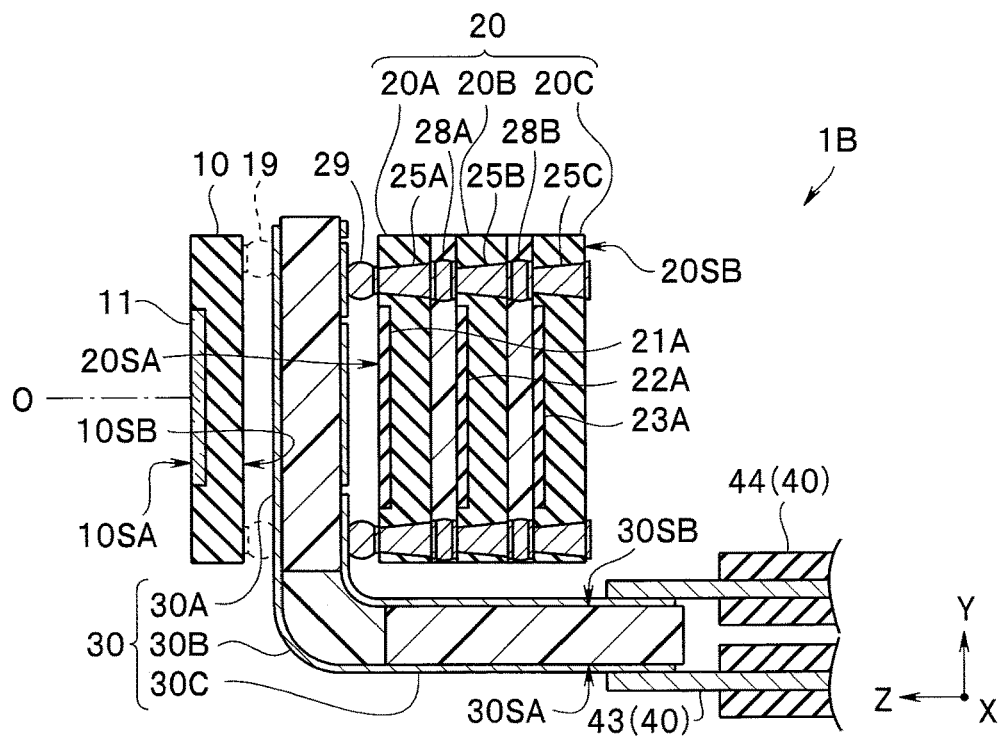
FIG. 9 is a cross-sectional view of an image pickup apparatus of a third embodiment.

In the image pickup apparatus 1B of the present embodiment shown in FIG. 9, the plurality of signal cables 40 include a third cable 43 bonded to the first principal surface 30SA and a fourth cable 44 bonded to the second principal surface 30SB.

In the image pickup apparatus 1B, a large part of heat of the stacked device 20 is transferred to the fourth cable 44 by way of the conductor layer of the second principal surface 30SB. A large part of heat of the image pickup device 10 is transferred to the third cable 43 by way of the conductor layer of the first principal surface 30SA.

In the image pickup apparatus 1B, a heat transfer path from the stacked device 20 and a heat transfer path from the image pickup device 10 are separated into the first principal surface 30SA and the second principal surface 30SB.

In the image pickup apparatus 1B, heat of the stacked device 20 is unlikely to be transferred to the image pickup device 10. Thus, the image pickup apparatus 1B enables a high-quality image to be obtained.

Note that it is also preferable in the image pickup apparatus 1B that the central section 30A should not have a through wiring having a small thermal resistance, in particular, a filled via.

Figure 10:
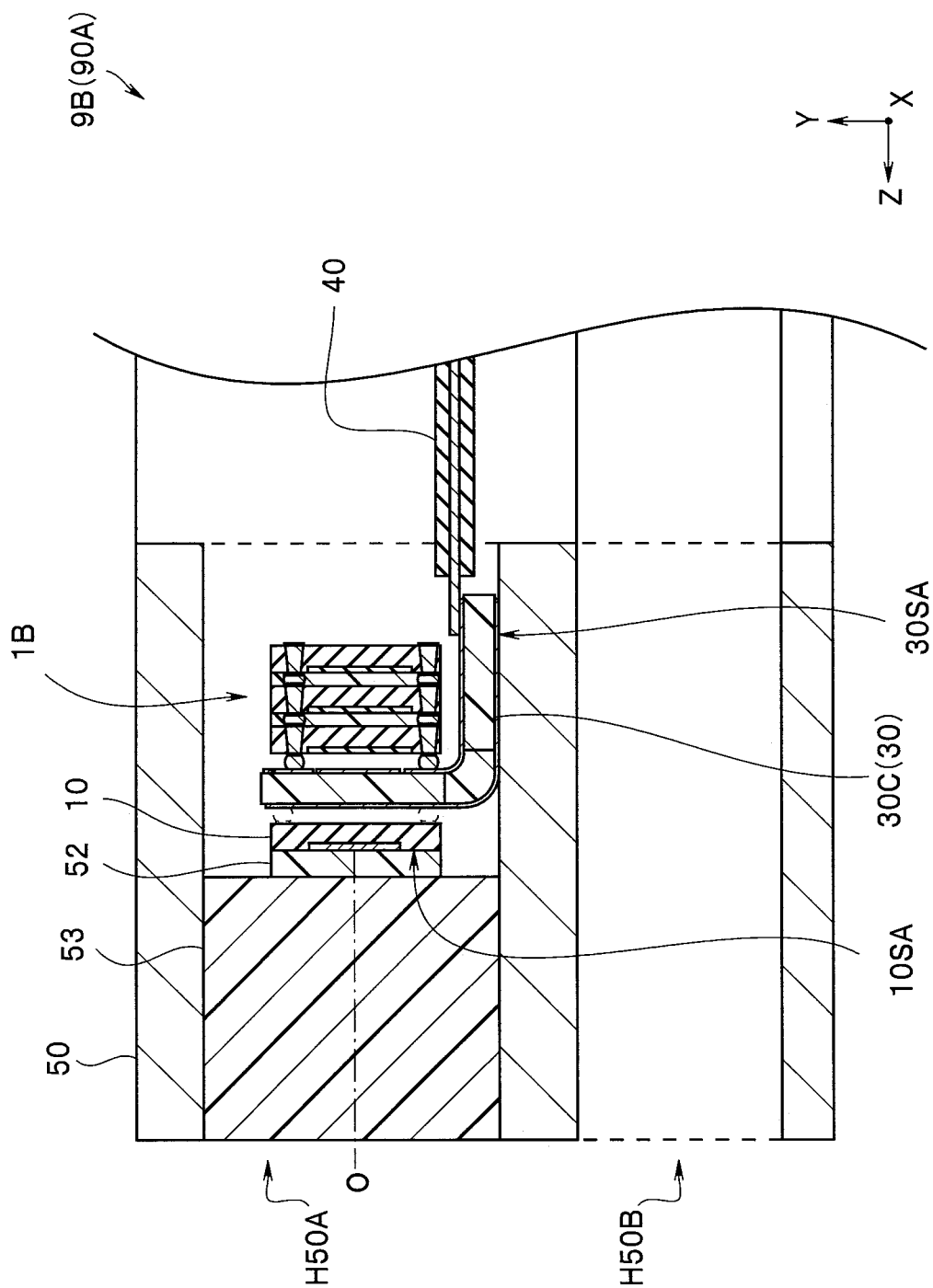
FIG. 10 is a cross-sectional view of a distal end portion of an endoscope including the image pickup apparatus of the third embodiment.

FIG. 10 is a cross-sectional view of the distal end portion 90A of an endoscope 9B including the image pickup apparatus 1B. A frame body 50 is disposed on the distal end portion 90A of the endoscope 9B. The frame body 50 made of stainless steel, for example, has a plurality of through holes H50A and H50B.

The image pickup optical system 53 including the cover glass 52 and a plurality of lenses is disposed on the light receiving surface 10SA of the image pickup apparatus 1B. The image pickup apparatus 1B is inserted into the first through hole H50A, and the first principal surface 30SA of the terminal section 30C of the wiring board 30 is in contact with the wall surface of the first through hole H50A. The conductor layer of the first principal surface 30SA is preferably at the ground potential.

Since the endoscope 9B can also transfer heat to the frame body 50 by way of the wiring board 30, heat transferred to the image pickup device 10 can be reduced further.

Note that a region of the wall surface of the first through hole H50A with which the wiring board 30 is in contact is a region proximate to the second through hole H50B other than the first through hole H50A into which the image pickup apparatus 1B is inserted. The through hole H50B is a channel or a water feeding pipe through which a treatment instrument is to be inserted, for example.

The endoscope 9B has a higher heat dissipation effect since the wiring board 30 is in contact with the region proximate to the second through hole H50B of the frame body 50.

Fourth Embodiment

Since an image pickup apparatus 1C of a fourth embodiment is similar to the image pickup apparatuses 1, 1A, and 1B, components having the same functions are denoted by the same reference characters, and description will be omitted.

Figure 11:
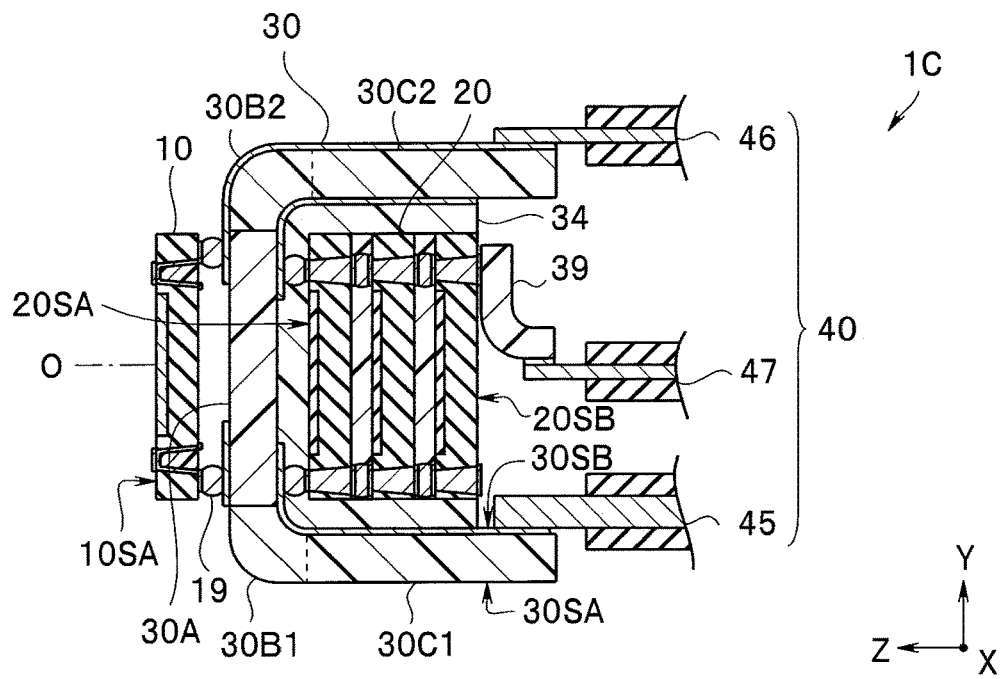
FIG. 11 is a cross-sectional view of an image pickup apparatus of a fourth embodiment.

The wiring board 30 of the image pickup apparatus 1C of the present embodiment shown in FIG. 11 includes the central section 30A having a substantially rectangular shape, a first intermediate section 30B1 that is extended from the central section 30A and is bent, a first terminal section 30B1 that is extended from the first intermediate section 30B1, a second intermediate section 30B2 that is extended from the central section 30A to the opposite side of the first intermediate section 30B1 and is bent, and a second terminal section 30C2 that is extended from the second intermediate section 30B2.

The wiring board 30 is a rigid-flexible wiring board in which only the central section 30A is non-flexible, and the first intermediate section 30B1, the second intermediate section 30B2, the first terminal section 30C1, and the second terminal section 30C2 are flexible. For example, the first intermediate section 30B1 and the first terminal section 30C1 are integral, and the boundary of the first intermediate section 30B1 and the first terminal section 30C1 is not clear.

The second intermediate section 30B2 is bent substantially at the right angle similarly to the first intermediate section 30B1, and the second terminal section 30C2 is arranged parallel to the first terminal section 30C1 so as to cover the side surface of the stacked device 20, and is secured by resin 34.

The plurality of signal cables 40 include a fifth cable 45 bonded to the second principal surface 30SB of the first terminal section 30C1 and a sixth cable 46 bonded to the first principal surface 30SA of the second terminal section 30C2. The plurality of signal cables 40 also include a seventh cable 47 connected to the back surface 20SB opposite to the bonding surface 20SA of the stacked device 20. The seventh cable 47 is bonded to a wiring board 39 bonded to the back surface 20SB.

In the image pickup apparatus 1C, a path along which heat generated from the stacked device 20 is transferred and a path along which heat generated from the image pickup device 10 is transferred are separated into the first intermediate section 30B1 and the first terminal section 30C1, and the second intermediate section 30B2 and the second terminal section 30C2. The two paths along which heat is transferred are further separated into the first principal surface 30SA and the second principal surface 30SB of the wiring board 30.

Note that the fifth cable 45 along which heat generated from the stacked device 20 is transferred has a conductor wire thicker than a conductor wire of the sixth cable 46 along which heat generated from the image pickup device 10 is transferred. For example, the fifth cable 45 is intended for power supply, and the sixth cable 46 is intended for signal transmission. The fifth cable 45 having the thick conductor wire has heat transfer performance higher than heat transfer performance of the sixth cable 46.

Note that in order to transfer a larger amount of heat to the fifth cable 45, a region of the wiring board to which the fifth cable 45 is bonded preferably has a wiring density higher than the wiring density of a region of the wiring board to which the sixth cable 46 is bonded.

Heat generated by the stacked device 20 is transferred from the back surface 20SB to the seventh cable 47.

In the image pickup apparatus 1C, heat generated from the stacked device 20 is unlikely to be transferred to the image pickup device 10. Thus, the image pickup apparatus 1C of the present embodiment enables a high-quality image to be obtained.

Also in the image pickup apparatuses 1, 1A, and 1B, the terminal section 30C may be flexible, and a signal cable may be connected to the back surface 20SB of the stacked device 20. Also in the image pickup apparatuses 1, 1A, and 1B, a signal cable among the plurality of signal cables 40 along which heat generated from the stacked device 20 is transferred may have a conductor wire thicker than a conductor wire of another signal cable.

Note that merely by separating the path along which heat generated from the stacked device 20 is transferred and the path along which heat generated from the image pickup device 10 is transferred into the first intermediate section 30B1 and the first terminal section 30C1, and the second intermediate section 30B2 and the second terminal section 30C2, heat is unlikely to be transferred from the stacked device 20 to the image pickup device 10. In other words, the signal cables 40 may be respectively bonded to the respective second principal surfaces 30SB of the first terminal section 30C1 and the second terminal section 30C2.

In other words, in the image pickup apparatus, the wiring board should only include two intermediate sections and two terminal sections, and a plurality of signal cables should only include the fifth cable bonded to the first terminal section between the two terminal sections and the sixth cable bonded to the second terminal section between the two terminal sections.

Fifth Embodiment

Since an image pickup apparatus 1D of a fifth embodiment is similar to the image pickup apparatuses 1 and 1A to 1C, components having the same functions are denoted by the same reference characters, and description will be omitted.

Figure 12:
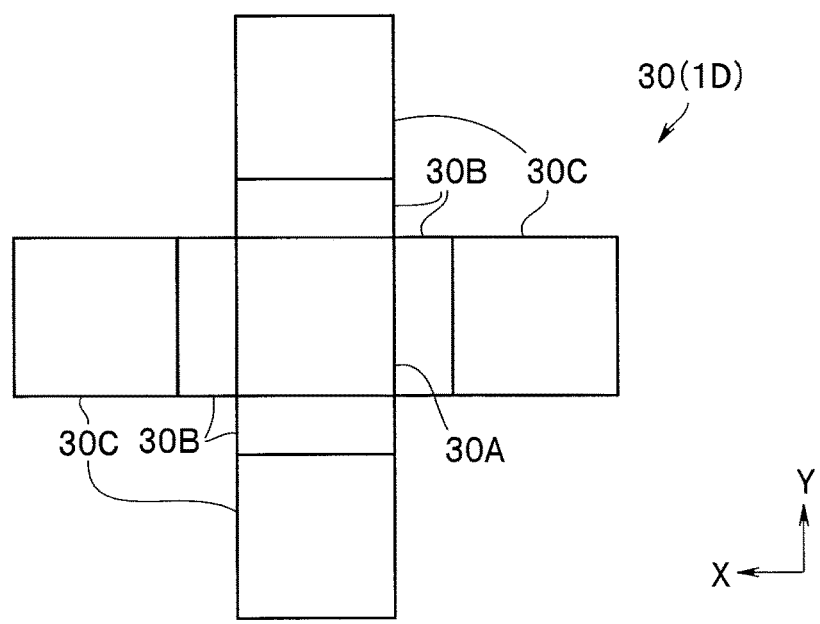
FIG. 12 is a schismatic plan view of a wiring board of an image pickup apparatus of a fifth embodiment.

As shown in FIG. 12, the wiring board 30 of the image pickup apparatus 1D has a cross shape centering on the central section 30A in a planar state. In other words, in the wiring board 30, the intermediate sections 30B are extended respectively from four end surfaces of the central section 30A having a substantially rectangular shape, and the terminal sections 30C are extended respectively from the four intermediate sections 30B.

Since the four intermediate sections 30B are bent at substantially 90 degrees although not shown, the four side surfaces of the stacked device 20 are covered by the respective terminal sections 30C.

In the image pickup apparatus 1D, the heal transfer paths are easy to separate. In the image pickup apparatus 1D, heat generated from the stacked device 20 is unlikely to be transferred to the image pickup device 10. Thus, the image pickup apparatus 1D enables a high-quality image to be obtained.

Note that the wiring board 30 may not have a cross shape in the planar state. Needless to say, even a wiring board having the three intermediate sections 30B and the three terminal sections 30C and having a T-shape in the planar state, for example, although not shown have the same effects as the effects of the wiring board 30 of the image pickup apparatus 1D.

In other words, if the wiring board includes a plurality of (two or more and four or less) intermediate sections and a plurality of (two or more and four or less) terminal sections, and the plurality of signal cables are bonded to the plurality of terminal sections, respectively, the image pickup apparatus enables a high-quality image to be obtained since heat generated from the stacked device 20 is unlikely to be transferred to the image pickup device 10.

Sixth Embodiment

Since an image pickup apparatus 1E of a sixth embodiment is similar to the image pickup apparatuses 1 and 1A to 1D, components having the same functions are denoted by the same reference characters, and description will be omitted.

Figure 13:
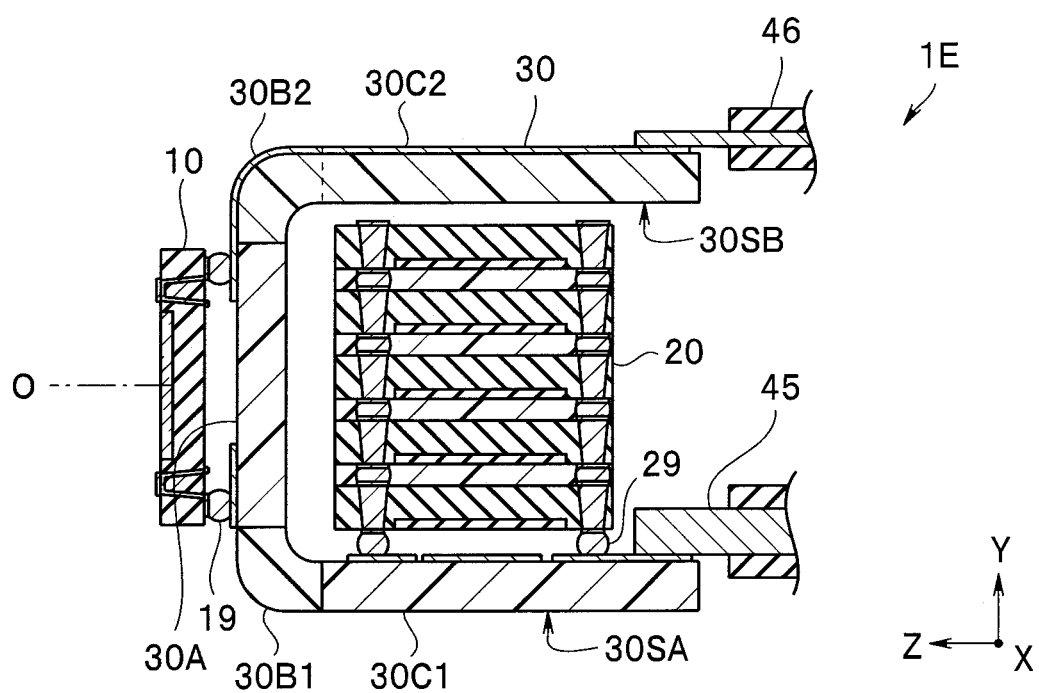
FIG. 13 is a cross-sectional view of an image pickup apparatus of a sixth embodiment.

The wiring board 30 of the image pickup apparatus 1E shown in FIG. 13 includes the central section 30A having a substantially rectangular shape, the first intermediate section 30B1 that is extended from the central section 30A and is bent, the first terminal section 30C1 that is extended from the first intermediate section 30B1, the second intermediate section 30B2 that is extended from the central section 30A to the opposite side of the first intermediate section 30B1 and is bent, and the second terminal section 30C2 that is extended from the second intermediate section 30B2.

The stacked device 20 is bonded to the second principal surface 30SB of the first terminal section 30C1. In other words, the plurality of semiconductor devices 20A to 20C of the stacked device 20 are stacked in a direction orthogonal to the optical axis direction.

The fifth cable 45 having a thick conductor wire for power supply use is bonded to an end portion of the second principal surface 30SB of the first terminal section 30C1. The sixth cable 46 for signal transmission use is bonded to an end portion of the first principal surface 30SA of the second terminal section 30C2.

Heat generated by the stacked device 20 is transferred to the fifth cable 45 by way of the conductor layer of the second principal surface of the first terminal section 30C1. A large part of heat generated by the image pickup device 10 is transferred to the sixth cable 46 by way of the conductor layer of the first principal surface 30SA of the second terminal section 30O2.

The image pickup apparatus 1E is not easy to make short and small since the stacked device 20 is bonded to the first terminal section 30C1. However, the heat transfer path from the stacked device 20 and the heat transfer path from the image pickup device 10 are completely separated. In the image pickup apparatus 1E, heat generated by the stacked device 20 is unlikely to be transferred to the image pickup device 10. Thus, the image pickup apparatus 1E enables a high-quality image to be obtained.

The fifth cable 45 having the thick conductor wire for power supply use is bonded to the second principal surface 30SB of the first terminal section 30C1, The sixth cable 46 for signal transmission use is bonded to the first principal surface 30SA of the second terminal section 30C2.

Note that the foregoing has described the image pickup apparatuses in which heat of the stacked device 20 is unlikely to be transferred to the image pickup device 10. The image pickup apparatuses of the invention interrupt not only heat transfer from the stacked device 20 to the image pickup device 10, but also heat transfer from the image pickup device 10 to the stacked device 20. Thus, the stacked device 20 is prevented from rising in temperature to destabilize the operation of the semiconductor circuits or to decrease reliability.

Note that in order to transfer heat of the image pickup device 10 to the wiring board 30 more efficiently, a gap between the image pickup device 10 and the wiring board 30 may be filled with a high thermal conductive resin containing an insulating filler such as silicon particles.

Needless to say, the endoscopes 9A to 9E respectively having the image pickup apparatuses 1A to 1E have effects of the respective image pickup apparatuses 1A to 1E in addition to the effects of the endoscope 9. In the endoscopes 9, 9A, 9C to 9E, the wiring board of each of the image pickup apparatuses is preferably in contact with the wall surface of the through hole of the frame body into which the image pickup apparatus is inserted as in the endoscope 9B. Although the image pickup apparatuses 1A to 1E are image pickup apparatuses for endoscope, the application of the image pickup apparatuses of the embodiments is not limited.

The invention is not limited to the aforementioned embodiments and the like, and various changes, modifications, and the like can be made within the range not departing from the gist of the invention.

What is claimed is:

1. An image pickup apparatus comprising:
   an image pickup member including an image pickup device;
   a stacked device in which a plurality of semiconductor devices are stacked;
   a wiring board including a first principal surface and a second principal surface opposite to the first principal surface, the wiring board including a central section including a substrate thicker than the image pickup device, at least one intermediate section that is extended from the central section and is bent, and at least one terminal section that is extended from the intermediate section, the image pickup member being bonded to the first principal surface of the central section, the stacked device being bonded to the second principal surface of the central section; and
   a plurality of signal cables bonded to the terminal section.

2. The image pickup apparatus according to claim 1, wherein
   the central section has a substrate containing resin and air, and
   the substrate contains 10% or more by volume of air.

3. The image pickup apparatus according to claim 1, wherein the wiring board has a through wiring formed only at a place other than the central section.

4. The image pickup apparatus according to claim 3, wherein
   the plurality of signal cables are bonded to the first principal surface or the second principal surface, and
   the plurality of signal cables include a first cable not bonded to the through wiring and a second cable bonded to the through wiring.

5. The image pickup apparatus according to claim 3, wherein the plurality of signal cables include a third cable bonded to the first principal surface and a fourth cable bonded to the second principal surface.

6. The image pickup apparatus according to claim 3, wherein
   the wiring board includes a plurality of intermediate sections and a plurality of terminal sections, and
   the plurality of signal cables are respectively bonded to the plurality of terminal sections.

7. The image pickup apparatus according to claim 6, wherein
   the wiring board includes two intermediate sections and two terminal sections, and
   the plurality of signal cables include a fifth cable bonded to a first terminal section and a sixth cable bonded to a second terminal section.

8. The image pickup apparatus according to claim 7, wherein the fifth cable is bonded to the second principal surface, and the sixth cable is bonded to the first principal surface.

9. The image pickup apparatus according to claim 1, wherein the plurality of signal cables include a seventh cable connected to a surface opposite to a surface of the stacked device bonded to the wiring board.

10. The image pickup apparatus according to claim 1, wherein a conductor layer covers 70% or more of the first principal surface and the second principal surface.

11. An endoscope comprising an image pickup apparatus, wherein
    the image pickup apparatus includes:
      an image pickup member including an image pickup device;
      a stacked device in which a plurality of semiconductor devices are stacked;
      a wiring board including a first principal surface and a second principal surface opposite to the first principal surface, the wiring board including a central section including a substrate thicker than the image pickup device, at least one intermediate section that is extended from the central section and is bent, and at least one terminal section that is extended from the intermediate section, the image pickup member being bonded to the first principal surface of the central section, the stacked device being bonded to the second principal surface of the central section; and
      a plurality of signal cables bonded to the terminal section.

12. The endoscope according to claim 11, comprising:
    a frame body including a plurality of through holes, wherein
    the wiring board is in contact with a wall surface of one through hole into which the image pickup apparatus is inserted, the one through hole being among the plurality of through holes.

13. The endoscope according to claim 12, wherein a region of the wall surface with which the wiring board is in contact is a region proximate to another through hole other than the one through hole into which the image pickup apparatus is inserted.

14. A method of manufacturing an image pickup apparatus comprising:
    fabricating an image pickup member including an image pickup device, a stacked device in which a plurality of semiconductor devices are stacked, and a wiring board including a first principal surface and a second principal surface opposite to the first principal surface, the wiring board including a central section including a substrate thicker than the image pickup device, an intermediate section that is extended from the central section, and a terminal section that is extended from the intermediate section;
    bonding the stacked device to the second principal surface of the central section of the wiring board;
    bending the intermediate section into a state that covers a side surface of the stacked device, and securing the intermediate section;
    bonding the image pickup member to the central section of the wiring board; and
    bonding a plurality of signal cables to the terminal section.

15. The method of manufacturing an image pickup apparatus according to claim 14, wherein when bonding the plurality of signal cables, a cable which is at a ground potential among the plurality of signal cables is initially bonded to the wiring board.

* * * * *